United States Patent [19]

Smith et al.

[11] 4,159,279
[45] Jun. 26, 1979

[54] NUCLEAR SUBSTITUTED 2-HYDROXYPHENYLMETHANESULFAMIC ACIDS

[75] Inventors: Robert L. Smith, Lansdale; Gerald E. Stokker, Gwynedd Valley; Edward J. Cragoe, Jr., Lansdale, all of Pa.

[73] Assignee: Merck & Co., Inc., Rahway, N.J.

[21] Appl. No.: 854,289

[22] Filed: Nov. 23, 1977

[51] Int. Cl.$^2$ .................................. C07C 143/86
[52] U.S. Cl. .................................. 260/513.6; 424/315
[58] Field of Search .................................. 260/513.6

[56] References Cited

U.S. PATENT DOCUMENTS

| 2,662,094 | 12/1953 | Kamlet | 260/513.6 |
| 3,794,734 | 2/1974 | Cragoe, Jr. et al | 424/330 |

OTHER PUBLICATIONS

Yamaguchi, Nippon Kagaku Zasshi, 89, 1099 (1968 (Chem. Abstract, 70, 96289v (1969)).

*Primary Examiner*—Nicky Chan
*Attorney, Agent, or Firm*—Michael C. Sudol, Jr.; Harry E. Westlake, Jr.

[57] ABSTRACT

Nuclear substituted 2-hydroxyphenylmethanesulfamic acids and their pharmaceutically acceptable salts wherein the phenyl nucleus is substituted with 2 to 4 nuclear substituents and which are useful saluretic-diuretics and anti-inflammatories are disclosed. The products may be prepared by reacting nuclear substituted salicylaldehydes with ammonium sulfamate to generate intermediate imines which are reduced to afford the compounds of this invention.

8 Claims, No Drawings

NUCLEAR SUBSTITUTED 2-HYDROXYPHENYLMETHANESULFAMIC ACIDS

SUMMARY OF THE INVENTION

This invention relates to a new class of chemical compounds which can be described generally as nuclear substituted 2-hydroxyphenylmethanesulfamic acids and to their non-toxic pharmaceutically acceptable salts.

Pharmacological studies indicate that the instant products are effective diuretic and saluretic agents which can be used in the treatment of conditions associated with electrolyte and fluid retention and hypertension. When administered in a therapeutic dosage in conventional vehicles, the instant products effectively reduce the amount of sodium and chloride ions in the body, lower dangerous excesses of fluid to acceptable levels, and, in general, alleviate conditions usually associated with edema and hypertension.

In addition, pharmacological studies indicate that the instant products of this invention are effective anti-inflammatory agents which can be used in the treatment of inflammation when administered topically, orally, rectally or parenterally. When applied topically, the instant products are particularly effective in the treatment of dermatological disorders and like conditions, such as dermititis (actimic, atopic, contact, eczematoid, seborrheic and stasis), herpetiformis, lichen planus, neurodermatitus, intitrigo, lichen simplex chronicus, and puritus, as well as for topical treatment of inflammation of the respiratory and intestinal mucosa, such as allergic rhinitus, bronchitis, bronchial asthma, bronchiectasis, colitis and the like.

The nuclear substituted 2-hydroxyphenylmethanesulfamic acids of this invention are compounds having the following structural formula:

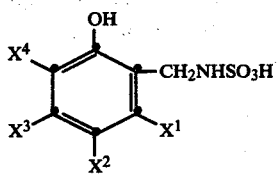

wherein
$X^1$ is hydrogen, lower alkyl of 1 to 3 carbon atoms, or lower alkoxy of 1 to 3 carbon atoms;
$X^2$ is halogen or straight or branched chain lower alkyl wherein the alkyl group has up to 5 carbon atoms;
$X^3$ is hydrogen, halogen, lower alkyl having up to 5 carbon atoms or lower alkoxy having up to 5 carbon atoms;
$X^4$ is halogen, trifluoromethyl or loweralkylthio wherein the alkyl group has 1 to 3 carbon atoms;
and the non-toxic pharmaceutically acceptable salts thereof.

A more preferred aspect of this invention is constituted by those compounds of Formula I wherein:
$X^1$ is hydrogen or lower alkoxy of 1 to 3 carbon atoms;
$X^2$ is halogen or branched chain lower alkyl wherein the alkyl group has 3 to 5 carbon atoms;
$X^3$ is hydrogen or lower alkoxy of 1 to 3 carbon atoms;
$X^4$ is halogen, trifluoromethyl or alkylthio wherein the alkyl group has 1 to 3 carbon atoms;
and the non-toxic pharmaceutically acceptable salts thereof.

A most preferred embodiment of this invention consists of those compounds of Formula I wherein:
$X^1$ and $X^3$ are hydrogen or methoxy;
$X^2$ is chloro, bromo, iodo or branched chain lower alkyl wherein the alkyl group has 3 to 5 carbon atoms;
$X^4$ is chloro, bromo, iodo, trifluoromethyl or methylthio;
and the non-toxic pharmaceutically acceptable salts thereof.

The non-toxic pharmaceutically acceptable salts mentioned above are those salts derived from the instant product sulfamic acids I and non-toxic pharmaceutically acceptable bases such as the alkalai metal and alkaline earth metal hydroxides and amines. Especially preferred metal cations are those derived from alkalai metals, e.g., sodium, potassium, lithium and the like, and alkaline earth metals, e.g., calcium, magnesium and the like, and other metals, i.e., aluminum, iron and zinc. Pharmaceutically acceptable cations derived from primary, secondary or tertiary amines, or quaternary ammonium hydroxides are methylamine, dimethylamine, trimethylamine, ethylamine, N-methylhexylamine, benzylamine, α-phenethylamine, ethylenediamine, piperidene, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethylammonium hydroxide, tetraethylammonium hydroxide, benzyltrimethylammonium hydroxide and the like.

Preferred specific compounds of this invention can be
2-hydroxy-3-iodo-5-(1,1-dimethylethyl)phenylmethanesulfamic acid;
2-hydroxy-3,5-diiodophenylmethanesulfamic acid;
2-hydroxy-3-trifluoromethyl-5-(1,1-dimethylethyl)-phenylmethanesulfamic acid;
2-hydroxy-3-methylthio-5-(1,1-dimethylethyl)phenylmethanesulfamic acid;
2-hydroxy-3,5-dichloro-4,6-dimethoxyphenylmethanesulfamic acid.

The nuclear substituted 2-hydroxyphenylmethanesulfamic acids of this invention of Formula I

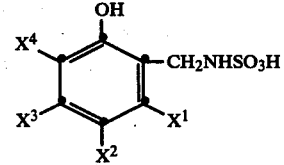

wherein $X^1$, $X^2$, $X^3$ and $X^4$ are as previously defined can be prepared by the following major synthetic method, Method A. A substituted salicylaldehyde of the formula

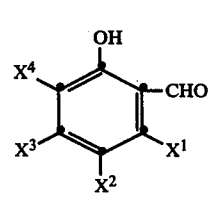

wherein $X^1$, $X^2$, $X^3$ and $X^4$ are as previously defined is made to react with ammonium sulfamate to give an intermediate imine of the formula

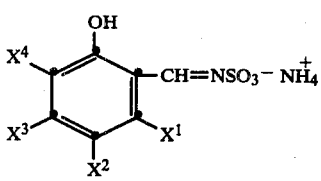
(III)

wherein $X^1$, $X^2$, $X^3$ and $X^4$ are as previously defined which, in turn, is reduced with an alkalai metal borohydride reagent to afford, after acidification, the instant products of this invention of Formula I. A detailed description of Method A follows.

(1) A substituted salicylaldehyde of Formula II wherein $X^1$, $X^2$, $X^3$ and $X^4$ are as previously defined is made to react with ammonium sulfamate in a suitable inert solvent, preferably methanol, ethanol and the like, at a temperature of 20° C. to the reflux temperature of the solvent, preferably 40° to 65° C., for a period of 1 to 4 hours, preferably 1½ to 2 hours, to generate in situ an intermediate imine of Formula III.

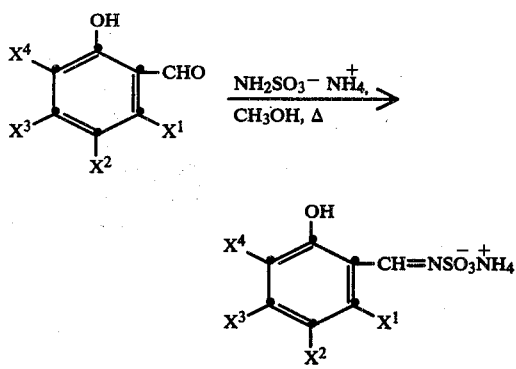

(2) An intermediate immine of Formula III wherein $X^1$, $X^2$, $X^3$ and $X^4$ are as previously defined is treated with a suitable alkalai metal borohydride reagent, preferably sodium or potassium borohydride, in a suitable solvent, preferably methanol, ethanol and the like, at a temperature of 0° to 40° C., preferably 20° to 25° C., for a period of 6 to 24 hours, preferably 12 to 20 hours, to afford, after acidification of the reaction mixture, the product 2-hydroxyphenylmethanesulfamic acid of Formula I.

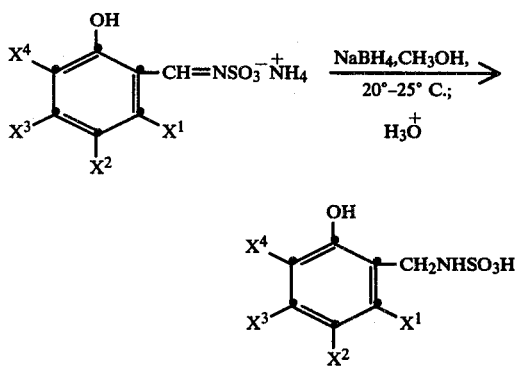

A subgroup of compounds of this invention of Formula IV

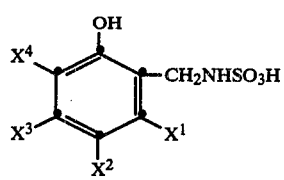
(IV)

wherein $X^1$, $X^2$ and $X^3$ are as previously defined and $X^4$ is chloro, bromo or iodo can be synthesized by an alternate synthetic method, Method B, which is described below.

A substituted salicylaldehyde of the formula

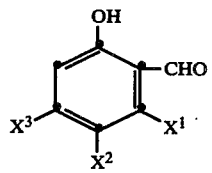
(V)

wherein $X^1$, $X^2$ and $X^3$ are as previously defined is made to react with ammonium sulfamate to give an intermediate imine of the formula

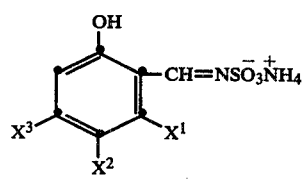
(VI)

wherein $X^1$, $X^2$ and $X^3$ are as previously defined which, in turn, is reduced with a suitable alkalai metal borohydride reagent to provide, after acidification, a sulfamic acid of the formula

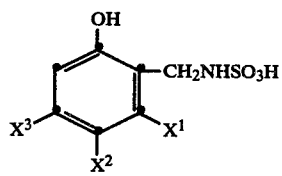
(VII)

wherein $X^1$, $X^2$ and $X^3$ are as previously defined and which, upon halogenation, affords a product of Formula IV. A detailed description of method B follows.

(1) A substituted salicylaldehyde of Formula V wherein $X^1$, $X^2$ and $X^3$ are as previously defined is made to react with ammonium sulfamate in exactly the same manner as described in equation (1) of Method A to give an intermediate imine of Formula VI.

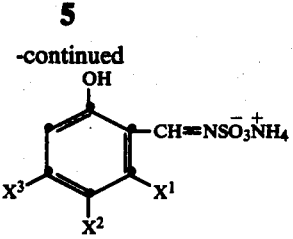
(VI)

(2) An intermediate imine of Formula VI wherein $X^1$, $X^2$ and $X^3$ are as previously defined is treated with a suitable alkalai metal borohydride reagent exactly as described in equation (2) of Method A to afford a sulfamic acid of Formula VII.

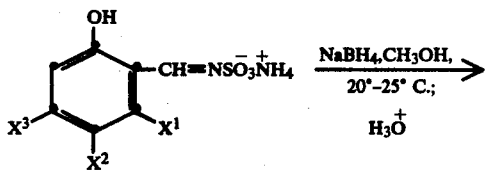
(VI)

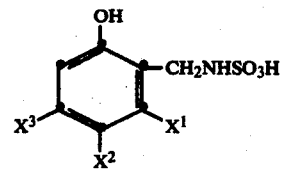
(VII)

(3) A sulfamic acid of Formula VII wherein $X^1$, $X^2$ and $X^3$ are as previously defined is treated with a suitable halogenation reagent of the formula $X^4$—Cl wherein $X^4$ is as previously defined, preferably iodine monochloride, bromine monochloride or chlorine, in a suitable protic acidic medium such as aqueous acetic acid, aqueous tetrahydrofuran and the like in the presence of an acid, preferably 3 N hydrochloric acid, at a temperature of 0° to 80° C., preferably about 20° C., for a period of 1 to 10 hours, preferably 2 to 4 hours, to afford a compound of Formula IV.

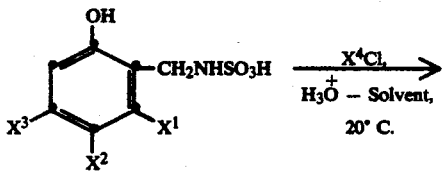
(VII)

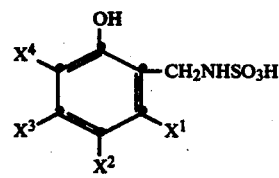
(IV)

Finally, those starting salicylaldehydes of the formula

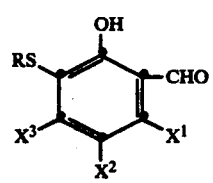
(VIII)

wherein $X^1$, $X^2$ and $X^3$ are as previously defined and R is an alkyl group having 1 to 3 carbon atoms and which are not currently known in the art but are required for their ultimate conversion to the instant products of this invention by Method A can be prepared by the following method. A phenol of the formula

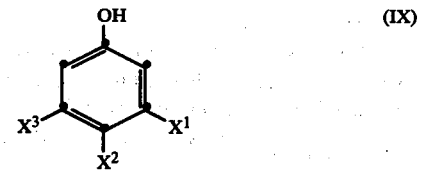
(IX)

wherein $X^1$, $X^2$ and $X^3$ are as previously defined is made to react with a dialkylsulfoxide of the formula RSOR wherein R is as previously defined in the presence of a strong acid to afford, after treatment with refluxing aqueous potassium chloride, a thioether of the formula

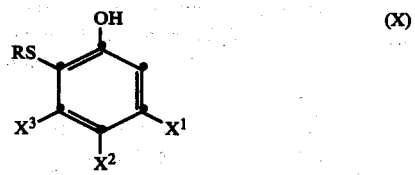
(X)

wherein $X^1$, $X^2$ and $X^3$ are as previously defined which is then amidomethylated and the resulting amide subsequently hydrolyzed to give a benzylamine hydrochloride of the formula

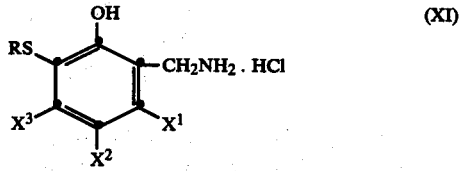
(XI)

which is treated with hexamethylenetetramine followed by acid hydrolysis to afford the desired salicylaldehyde of Formula VIII. Details of this method follow.

(1) A phenol of Formula IX wherein $X^1$, $X^2$ and $X^3$ are as previously defined is reacted with a dialkylsulfoxide of the formula RSOR such as dimethylsulfoxide and the like in the presence of a suitable dehydrating agent, preferably phosphorous oxychloride, in a suitable acidic medium, preferably 70% perchloric acid, at a temperature of 0° to 40° C., preferably about 20° C., for a period of 12 to 24 hours, preferably 15 to 18 hours, to give an intermediate adduct which upon treatment with a saturated aqueous solution of an alkalai metal halide, preferably sodium or potassium chloride, at the reflux temperature of the solution for a period of 2 to 6 hours, preferably about 4 hours, provides a thioether of Formula X.

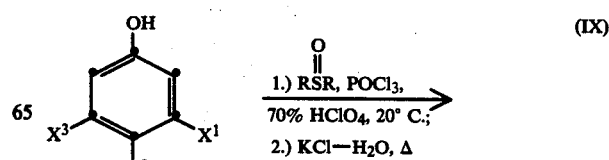
(IX)

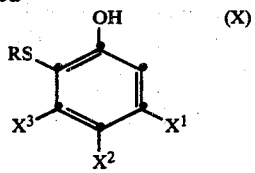

(2) A thioether of Formula X wherein $X^1$, $X^2$, $X^3$ and R are as previously defined is amidomethylated using a suitable N-hydroxymethylamide of the formula

HOCH₂NHR¹ wherein $R^1$ is an acyl moiety, preferably 2,2,2-trifluoroacetyl, 2,2,2-trichloroacetyl or 2-chloroacetyl, in the presence of a mineral acid to give an intermediate amide which upon hydrolysis in an acidic medium, preferably ethanol 12 N hydrochloric acid, affords a benzylamine hydrochloride of Formula XI. The details of this amidomethylation-hydrolysis step are described in U.S. Pat. No. 4,029,816 which issued June 14, 1977.

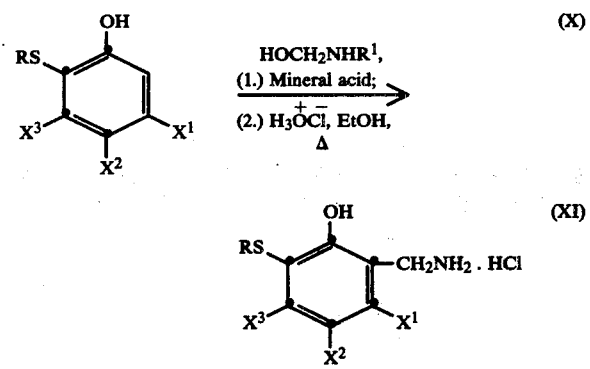

(3) A benzylamine hydrochloride of Formula XI wherein $X^1$, $X^2$, $X^3$ and R are as previously described is treated with hexamethylenetetramine in a suitable acidic medium, preferably aqueous acetic acid, at the reflux temperature of the medium for a period of 2 to 12 hours, preferably about 4 hours, followed by treatment with a strong mineral acid, preferably hydrochloric acid, at the reflux temperature of the reaction mixture for a brief period, preferably 10 to 30 minutes, to afford a salicylaldehyde of Formula VIII.

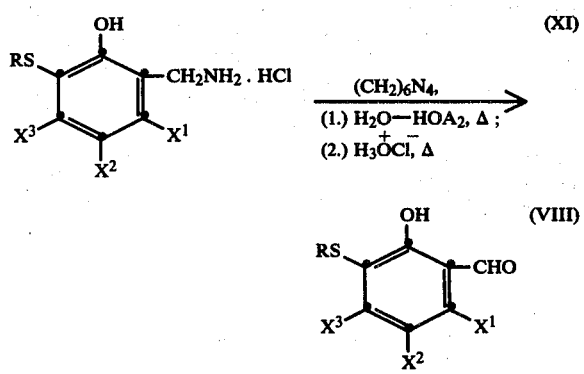

The examples which follow illustrate the nuclear substituted 2-hydroxyphenylmethanesulfamic acids of this invention and the methods by which they are prepared.

EXAMPLE 1

Preparation of 2-Hydroxy-3-iodo-5-(1,1-dimethylethyl)phenylmethanesulfamic acid

Step A. Preparation of 2-Hydroxy-5-(1,1-dimethylethyl)phenylmethanesulfamic acid A solution of 5-(1,1-dimethylethyl)salicylaldehyde (3.56 g., 0.02 mole) and ammonium sulfamate (2.28 g., 0.02 mole) in anhydrous methanol (100 ml.) is stirred and heated at reflux for 1½ hours. The resulting clear, yellow solution is cooled to 5°–10° C., treated with sodium borohydride (0.76 g., 0.02 mole) added portionwise over 5 minutes and stirred at 20° C. for 20 hours. Evaporation of the solvent in vacuo leaves a residue which is treated with water (150 ml.). The resulting heterogeneous mixture is cooled to 0°–5° C., cautiously acidified with 12 N hydrochloric acid and filtered to give 2.3 g. (44.3%) of 2-hydroxy-5-(1,1-dimethylethyl)phenylmethanesulfamic acid, m.p. 260°–262° C. with dec. Recrystallization from ethertetrahydrofuran (5:1; v:v) affords an analytical sample of 2-hydroxy-5-(1,1-dimethylethyl)phenylmethanesulfamic acid as colorless crystals, m.p. 264°–265° C. with dec.

Step B. Preparation of 2-Hydroxy-3-iodo-5-(1,1-dimethylethyl)phenylmethanesulfamic acid To a solution of 2-hydroxy-5-(1,1-dimethylethyl)phenylmethanesulfamic acid (2.6 g., 0.01 mole) in water-tetrahydrofuran (5:1; v:v; 90 ml.) is added a freshly prepared solution of iodine monochloride (1.64 g., 0.01 mole) in 3 N hydrochloric acid (12 ml.) portionwise over 5 minutes providing a dark reaction solution which is stirred at 20° C. for 2 hours and then cooled to 0°–5° C. The resulting insoluble solid is collected, washed with 12 N hydrochloric acid, dried with aspiration at 20° C. and washed with water to give crude 2-hydroxy-3-iodo-5-(1,1-dimethylethyl)phenylmethanesulfamic acid (3.3 g., 85.9%), m.p. 172°–180° C. with dec. Recrystallization from water-ethanol (10:1; v:v) provides pure 2-hydroxy-3-iodo-5-(1,1-dimethylethyl)phenylmethanesulfamic acid as colorless crystals, m.p. 180°–182° C. with dec.

EXAMPLE 2

Preparation of 2-Hydroxy-3,5-diiodophenylmethanesulfamic acid. Ethanol Solvate

Step A: Preparation of 2-Hydroxyphenylmethanesulfamic acid

This compound is prepared essentially by the same method as described in Example 1, Step A, except that the 5-(1,1-dimethylethyl)salicylaldehyde is replaced by salicylaldehyde. The following reagents are employed:
salicylaldehyde—4.6 g., 0.038 mole
ammonium sulfamate—4.0 g., 0.035 mole
methanol—100 ml.
sodium borohydride—1.44 g., 0.038 mole.

Concentration of the reduction mixture leaves a residual solid which is dissolved in water (400 ml.). The resulting solution is treated with 12 N hydrochloric acid (5 ml.) and filtered to provide an aqueous solution of 2-hydroxyphenylmethanesulfamic acid which is used directly in Step B described below without further purification.

Step B. Preparation of
2-Hydroxy-3,5-diiodophenylmethanesulfamic acid.
Ethanol Solvate To the aqueous solution of 2-hydroxyphenylmethanesulfamic acid (ca. 0.035 mole) described in Step A above is added a freshly prepared solution of iodine monochloride (11.37 g., 0.070 mole) in 3 N hydrochloric acid (60 ml.) portionwise over 5 minutes. The resulting reaction mixture is stirred at 20° C. for 16 hours and filtered. The collected pale yellow solid is washed with 12 N hydrochloric acid, air-dried with aspiration, washed with ether and crystallized from ether-ethanol (14:1; v:v; 300 ml.) to afford 2-hydroxy-3,5-diiodophenylmethanesulfamic acid . ethanol solvate as pale yellow crystals (10.5 g., 60%), m.p. 168°–170° C. with dec. Recrystallization from ether-ethanol (8:1; v:v) gives analytically pure 2-hydroxy-3,5-diiodophenylmethanesulfamic acid . ethanol solvate, m.p. 172°–173° C. with dec.

EXAMPLE 3

Alternate Preparation of
2-Hydroxy-3-iodo-5-(1,1-dimethylethyl)phenylmethanesulfamic Acid Step A: Preparation of
3-Iodo-5-(1,1-dimethylethyl)salicylaldehyde To a solution of 2-aminomethyl-4-(1,1-dimethylethyl)-6-iodophenol hydrochloride (51.3 g., 0.15 mole) in acetic acid-water (11:3; v:v; 1.4 l.) is added a solution of hexamethylenetetramine (22.05 g., 0.158 mole) in water (75 ml.) providing a clear solution which is stirred and heated at reflux for 4 hours. The reaction mixture is treated with 4.5 N hydrochloric acid (225 ml.) and heated at reflux for 15 minutes. Upon slowly cooling to $-10°$ C., the 3-iodo-5-(1,1-dimethylethyl)salicylaldehyde is deposited as pale yellow crystals (20.4 g., 44.7%), m.p. 76°–78° C. Sublimation gives analytically pure 3-iodo-5-(1,1-dimethylethyl)salicylaldehyde, m.p. 77° C.

Step B: Preparation of
2-Hydroxy-3-iodo-5-(1,1-dimethylethyl)phenylmethanesulfamic acid This compound is prepared essentially by the same method as described in Example 1, Step A, except that the 5-(1,1-dimethylethyl)salicylaldehyde is replaced by 3-iodo-5-(1,1-dimethylethyl)salicylaldehyde. The following reagents are employed:

| | |
|---|---|
| 3-iodo-5-(1,1-dimethylethyl)-salicylaldehyde | 6.08 g., 0.02 mole |
| ammonium sulfamate | 2.28 g., 0.02 mole |
| methanol | 100 ml. |
| sodium borohydride | 0.76 g., 0.02 mole |
| water | 150 ml. |
| 12N hydrochloric acid | |
| ether-tetrahydrofuran (5:1; v:v) | |

This procedure affords analytically pure 2-hydroxy-3-iodo-5-(1,1-dimethylethyl)phenylmethanesulfamic acid, m.p. 180°–182° C. with dec., which is identical with the authentic 2-hydroxy-3-iodo-5-(1,1-dimethylethyl)phenylmethanesulfamic acid described in Example 1, Step B.

EXAMPLE 4

Preparation of
2-hydroxy-3-bromo-5-(1,1-dimethylethyl)phenylmethanesulfamic acid By following essentially the same procedures described in Example 3 but beginning with 2-aminomethyl-4-(1,1-dimethylethyl)-6-bromophenol hydrochloride instead of 2-aminomethyl-4-(1,1-dimethylethyl)-6-iodophenol hydrochloride, there are obtained successively, Step A, 3-bromo-5-(1,1-dimethylethyl)salicylaldehyde; Step B, 2-hydroxy-3-bromo-5-(1,1-dimethylethyl)phenylmethanesulfamic acid.

EXAMPLE 5

Preparation of
2-Hydroxy-3-chloro-5-(1,1-dimethylethyl)phenylmethanesulfamic acid By following essentially the same procedures described in Example 3 but beginning with 2-aminomethyl-4-(1,1-dimethylethyl)-6-chlorophenol hydrochloride instead of 2-aminomethyl-4-(1,1-dimethylethyl)-6-iodophenol hydrochloride, there are obtained successively: Step A, 3-chloro-5-(1,1-dimethylethyl)salicylaldehyde; Step B, 2-hydroxy-3-chloro-5-(1,1-dimethylethyl)phenyl-methanesulfamic acid.

EXAMPLE 6

Preparation of
2-Hydroxy-3-trifluoromethyl-5-(1,1-dimethylethyl)-phenylmethanesulfamic acid This compound is prepared essentially by the same method described in Example 1, Step A, except that the 5-(1,1-dimethylethyl)salicylaldehyde is replaced by 3-trifluoromethyl-5-(1,1-dimethylethyl)salicylaldehyde. Thereby is obtained 2-hydroxy-3-trifluoromethyl-5-(1,1-dimethylethyl)phenylmethanesulfamic acid.

EXAMPLE 7

Preparation of
2-Hydroxy-3,5-dichloro-4,6-dimethoxyphenylmethanesulfamic acid

This compound is prepared essentially by the same procedure as described in Example 1, Step A, except that the 5-(1,1-dimethylethyl)salicylaldehyde is replaced by 3,5-dichloro-4,6-dimethoxysalicylaldehyde. Thereby is obtained 2-hydroxy-3,5-dichloro-4,6-dimethoxyphenylmethanesulfamic acid.

EXAMPLE 8

Preparation of
2-Hydroxy-3-methylthio-5-(1,1-dimethylethyl)phenyl-methanesulfamic acid Step A: Preparation of
2-Methylthio-4-(1,1-dimethylethyl)phenol To a cold (0°–5° C.) suspension of 4-(1,1-dimethylethyl)phenol (7.5 g., 0.05 mole) and phosphorous oxychloride (8 ml.) in 70% perchloric acid (10 ml.) is added dimethylsulfoxide (3.9 g., 0.05 mole) dropwise with vigorous stirring. The resulting reaction mixture is stirred at 0°–5° C. for 1 hour and at 20° C. for 16 hours and then poured onto crushed ice whereupon a gum separates. Upon warming to 20° C. with vigorous stirring there is obtained a white solid which is collected, washed with cold water, air dried at 20° C. with aspiration and washed with ether. The white solid (10 g., m.p. 160° C.) is added to saturated aqueous potassium chloride (100 ml.) and the resulting mixture, heated at reflux for 4 hours. After standing at 20° C. for 12 hours, the reaction mixture is extracted with ether. The ethereal extract is washed with water and saturated brine, dried over sodium sulfate and filtered. Evaporation of the filtrate in vacuo leaves 2-methylthio-4-(1,1-dimethylethyl)phenol as an analytically pure, colorless oil (5.7 g., 58%).

Elemental analysis for $C_{11}H_{16}OS$ : Calc.: C, 67.30; H, 8.22. Found: C, 66.91, H, 8.22.

Step B. Preparation of 2-Aminomethyl-4-(1,1-dimethylethyl)-6-(methylthio)-phenol.hydrochloride Pulverized N-hydroxymethyl-2-chloroacetamide (3.32 g., 0.027 mole) is added portionwise over 15 minutes to a solution of 2-methylthio-4-(1,1-dimethylethyl)-phenol (5.3 g., 0.027 mole) and conc. sulfuric acid (10 ml.) in acetic acid (150 ml.) cooled in an ice bath. The resulting reaction mixture is stirred at 20° C. for 16 hours and then poured into ice-water (1 l.) whereupon a white gum is deposited. The gum is extracted with ether and the etheral extract, washed well with water and saturated brine. Removal of the solvent under reduced pressure leaves a residual solid which is dissolved in ethanol (30 ml.). The resulting solution is treated with 12 N hydrochloric acid (15 ml.) and heated at reflux for 4 hours. Evaporation in vacuo affords a residual solid which is triturated with ether and collected by filtration to give crude 2-aminomethyl-4-(1,1-dimethylethyl)-6-(methylthio)phenol hydrochloride (5.4 g., 76.4%), m.p. 150°–177° C. Two recrystallizations from ether-ethanol (10:1; v:v) followed by recrystallization from 12 N hydrochloric acid provides analytically pure 2-aminomethyl-4-(1,1-dimethylethyl)6-(methylthio)-phenol hydrochloride as colorless crystals, m.p. 180°–181.5° C.

Step C: Preparation of 3-Methylthio-5-(1,1-dimethylethyl)salicylaldehyde

This compound is prepared essentially by the same procedure as described in Example 3, Step A, except that the 2-aminomethyl-4-(1,1-dimethylethyl)-6-iodo-phenol hydrochloride is replaced by 2-aminomethyl-4-(1,1-dimethylethyl)-6-(methylthio)phenol hydrochloride. Thereby is obtained 3-methylthio-5-(1,1-dimethylethyl)salicylaldehyde.

Step D: Preparation of 2-Hydroxy-3-methylthio-5-(1,1-dimethylethyl)phenyl-methanesulfamic acid This compound is prepared essentially by the same procedure as described in Example 1, Step A, except that the 5-(1,1-dimethylethyl)salicylaldehyde is replaced by 3-methylthio-5-(1,1-dimethylethyl)-salicylaldehyde. Thereby is obtained 2-hydroxy-3-methylthio-5-(1,1-dimethylethyl)phenylmethanesulfamic acid.

The novel compounds of this invention are diuretic and saluretic agents which can be administered in a wide variety of therapeutic dosages in conventional vehicles as, for example, by oral administration in the form of a tablet or by intravenous injection. Also, the daily dosage of the products may be varied over a wide range varying from 5 to 2,000 mg. The product is preferably administered in subdivided doses in the form of scored tablets containing 5, 10, 25, 50, 100, 150, 250 and 500 milligrams of the active ingredient for the symptomatic adjustment of the dosage to the patient to be treated. These dosages are well below the toxic or lethal dose of the products which may be administered in a total daily dosage of from 100 mg. to 2,000 mg. in a pharmaceutically acceptable carrier.

A suitable unit dosage form of the products of this invention can be administered by mixing 50 milligrams of a nuclear substituted 2-hydroxyphenylmethanesulfamic acid (I) or a suitable salt thereof, with 149 mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules and, should it be necessary to mix more than 200 mg. of ingredients together, larger capsules may be employed. Compressed tablets, pills, or other desired unit dosages can be prepared to incorporate the compounds of this invention by conventional methods and, if desired, can be made up as elixirs or as injectable solutions by methods well known to pharmacists.

The following example is included to illustrate the preparation of a representative dosage form:

EXAMPLE 9

| Dry-filled capsules containing 50 mg. of active ingredient per capsule | |
|---|---|
| | Per Capsule |
| 2-hydroxy-3-iodo-5-(1,1-dimethyl-ethyl)phenylmethanesulfamic acid | 50 mg. |
| lactose | 149 mg. |
| magnesium stearate | 1 mg. |
| Capsule (Size No. 1) | 200 mg. |

The 2-hydroxy-3-iodo-5-(1,1-dimethylethyl)phenyl-methanesulfamic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other novel compounds of this invention.

What is claimed is:

1. A compound of the formula:

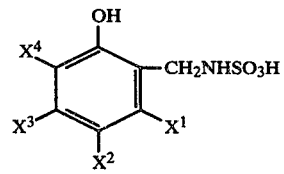

wherein
$X^1$ is
   hydrogen;
   lower alkyl;
   lower alkoxy;
$X^2$ is
   halogen or
   straight or branched chain lower alkyl;
$X^3$ is
   hydrogen;

halogen;
lower alkyl or
lower alkoxy;
$X^4$ is
halogen;
trifluoromethyl or
lower alkyl thio
and the non-toxic pharmaceutically acceptable salts thereof.

2. A compound of the formula:

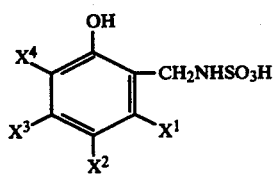

wherein
$X^1$ is
hydrogen,
alkoxy wherein the alkyl group has 1–3 carbon atoms;
$X^2$ is
halogen,
branched chain alkyl wherein the alkyl group has 3 to 5 carbon atoms;
$X^3$ is
hydrogen,
lower alkoxy having 1 to 3 carbon atoms;
$X^4$ is
halogen,
trifluoromethyl,
alkyl thio wherein the alkyl group has 1 to 3 carbon atoms; and
the non-toxic pharmaceutically acceptable salts thereof.

3. A compound of the formula:

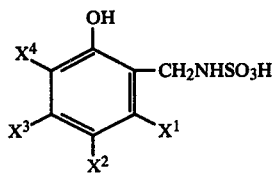

wherein
$X^1$ is
hydrogen or methoxy,
$X^2$ is
chloro, iodo or branched chain lower alkyl wherein the alkyl group has 3 to 5 carbon atoms;
$X^3$ is
hydrogen or methoxy;
$X^4$ is
chloro, bromo, iodo, trifluoromethyl or methylthio; and
the non-toxic pharmaceutically acceptable salts thereof.

4. A compound according to claim 3 which is 2-hydroxy-3-iodo-5-(1,1-dimethylethyl)phenylmethanesulfamic acid.

5. A compound according to claim 3 which is 2-hydroxy-3,5-diiodophenylmethanesulfamic acid.

6. A compound according to claim 3 which is 2-hydroxy-3-trifluoromethyl-5-(1,1-dimethylethyl)-phenylmethanesulfamic acid.

7. A compound according to claim 3 which is 2-hydroxy-3-methylthio-5-(1,1-dimethylethyl)phenylmethanesulfamic acid.

8. A compound according to claim 3 which is 2-hydroxy-3,5-dichloro-4,6-dimethoxyphenylmethanesulfamic acid.

* * * * *